United States Patent [19]
Rubinstein et al.

[11] Patent Number: 5,300,059
[45] Date of Patent: Apr. 5, 1994

[54] BLOODBAG AND METHOD OF MAKING SAME

[75] Inventors: Arye Rubinstein, Monsey, N.Y.; Albert Goldstein, Trenton Falls, N.J.; Howard I. Podell, New Rochelle, N.Y.

[73] Assignees: Hydro Slip Technologies Inc., Howell, N.J.; Albert Einstein College of Medicine, New York, N.Y.

[21] Appl. No.: 794,381

[22] Filed: Nov. 19, 1991

[51] Int. Cl.$^5$ .............................................. A61J 1/00
[52] U.S. Cl. .................................. 604/408; 604/403; 128/896
[58] Field of Search ................. 128/832, 846; 424/78.24, 78.01, 78.07, 78.06, 430; 604/408, 349, 403, 411

[56] References Cited

U.S. PATENT DOCUMENTS

| | | | |
|---|---|---|---|
| 3,520,949 | 7/1970 | Shepherd et al. | 240/857 |
| 3,566,874 | 3/1971 | Shepherd et al. | 128/349 |
| 3,598,127 | 8/1971 | Wepsic | 128/349 |
| 3,695,921 | 10/1972 | Shepherd et al. | 117/72 |
| 3,813,695 | 6/1974 | Podell, Jr. et al. | 2/168 |
| 4,482,577 | 11/1984 | Goldstein et al. | 427/2 |
| 4,548,844 | 10/1985 | Podell et al. | 428/35 |
| 4,575,476 | 3/1986 | Podell et al. | 428/494 |
| 4,771,482 | 9/1988 | Shlenker | 2/161 |
| 4,853,978 | 8/1989 | Stockum | 2/167 |
| 4,880,839 | 11/1989 | Tucker | 514/613 |
| 4,919,966 | 4/1990 | Shlenker | 427/2 |
| 4,932,948 | 6/1990 | Kernes et al. | 604/349 |
| 4,944,920 | 7/1990 | Rubinstein | 422/37 |
| 5,013,769 | 5/1991 | Murray et al. | 424/78.06 |
| 5,061,487 | 10/1991 | Blank et al. | 424/430 X |
| 5,080,902 | 1/1992 | Allenmark et al. | 434/430 |
| 5,137,718 | 8/1992 | Gillespie | 424/78.24 |
| 5,143,731 | 9/1992 | Viegas et al. | 424/430 X |

Primary Examiner—Robert A. Hafer
Assistant Examiner—Sam Rimell
Attorney, Agent, or Firm—David P. Gordon

[57] ABSTRACT

The interior surface of a container, such as a bloodbag, is primed and subsequently coated with a time-releasable viricide against HIV absorbed in a hydrogel polymer. The viricides of this invention are derivatives of urea, and upon release into the blood, have no adverse effects on the red blood cell functions of the blood.

41 Claims, 2 Drawing Sheets

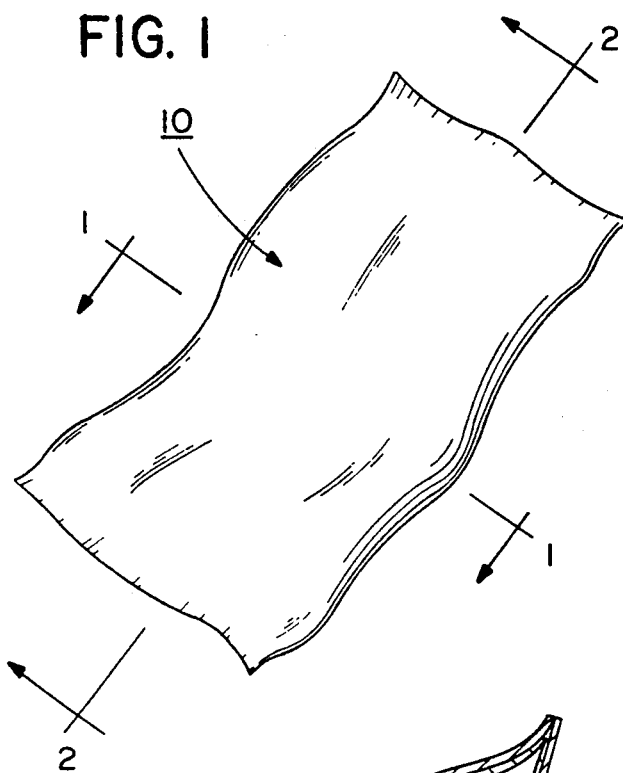
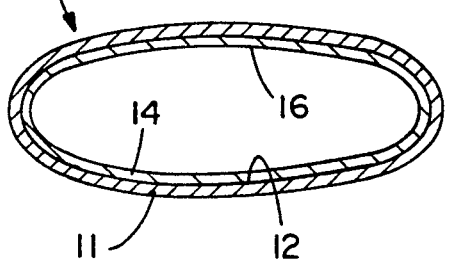
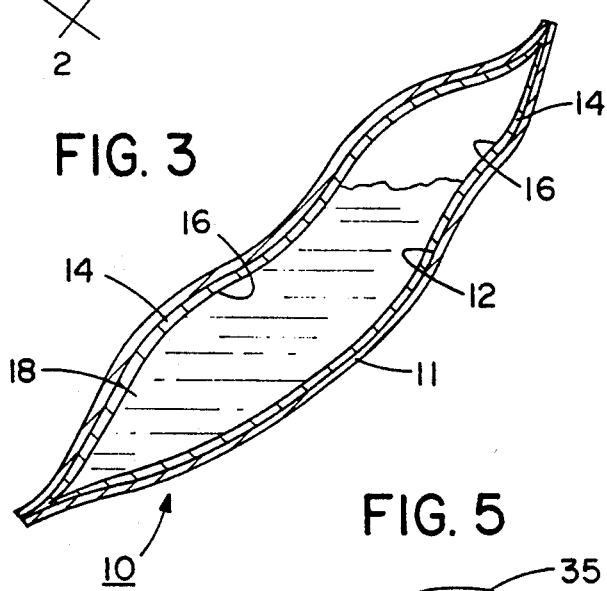
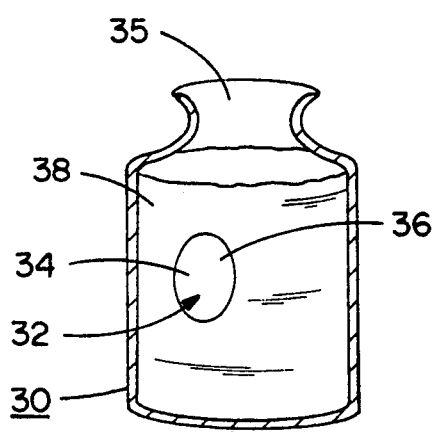
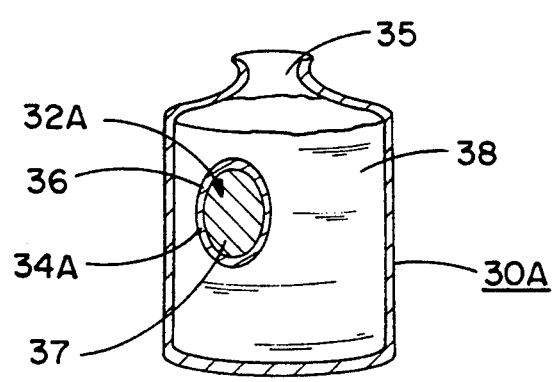

BLOODBAG AND METHOD OF MAKING SAME

FIELD OF THE INVENTION

This invention relates to an improved container for the storage of blood (a bloodbag) and more particularly to a viricide coated container which is capable of time-release of such viricide. This invention further relates to methods of making such a container and to novel viricides.

BACKGROUND OF THE INVENTION

To date, the risk of infection by the Human Immunodeficiency Virus (HIV) through transfusion of contaminated blood products has not been eliminated by serological screening of donors. Therefore, the need remains to minimize or eliminate the risk of infection with HIV of blood product recipients.

An object of this invention is to provide a product which eliminates the risk of HIV infection of blood product recipients.

Another object is to provide such a product which is reliable, economically efficient and simple to prepare.

A further object is to provide new viricides which do not impair the red blood cell functions of stored blood.

Other uses and advantages of this invention are described below.

SUMMARY OF THE INVENTION

The above and related objects of the present invention are obtained in an improved viricide coated container, such as a bloodbag, which is internally coated with a time releasable viricide against HIV. The viricide-coated container is prepared by priming a conventional plastic substrate film of which the container walls have been or will be made so as to activate the film. Next, the film is coated with a hydrogel polymer. A viricide is absorbed into the hydrogel polymer either prior to coating the film with the hydrogel polymer or after coating the film with the hydrogel polymer and curing the film. Conventional viricides may be used. However, a preferred viricide is an alkylurea, a hydroxyurea, acetyl pyridium chloride or a combination thereof. Alkylureas and hydroxyureas have no adverse affects on the red blood cells contained in the blood.

In a preferred embodiment of this invention, the substrate film is polyvinyl chloride film. The substrate film is primed using flame, oxidizing acid, corona discharge, plasma or coating with a primer. The coating primer may be a reactive resin, an oligomer or a salt solution of polyvalent ions. The viricide is preferably a urea derivative, such as a hydroxyurea or an alkylurea. Further, the viricide may be acetyl pyridium chloride. The hydrogel polymer is a copolymer of either hydroxyalkyl acrylates and methacrylates or acrylic and methacrylic acids. The hydrogel polymer may also be a mixture of hydrophilic monomers, a cellulose ester system or a polyurethane system. The container may be in the form of a bloodbag, a glove or a condom.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawing wherein:

FIG. 1 is a plan view of the bloodbag of this invention;

FIG. 2 is a cross-section of the bloodbag of this invention taken along line 1—1 of FIG. 1;

FIG. 3 is a cross-section of the bloodbag of this invention taken along line 2—2 of FIG. 1;

FIG. 4 is a cross-section of an alternative embodiment of the bloodbag of this invention;

FIG. 5 is a cross-section of a further embodiment of the bloodbag of this invention;

DETAILED DESCRIPTION OF THE PREFERRED EMBODIMENTS

Figure 6:
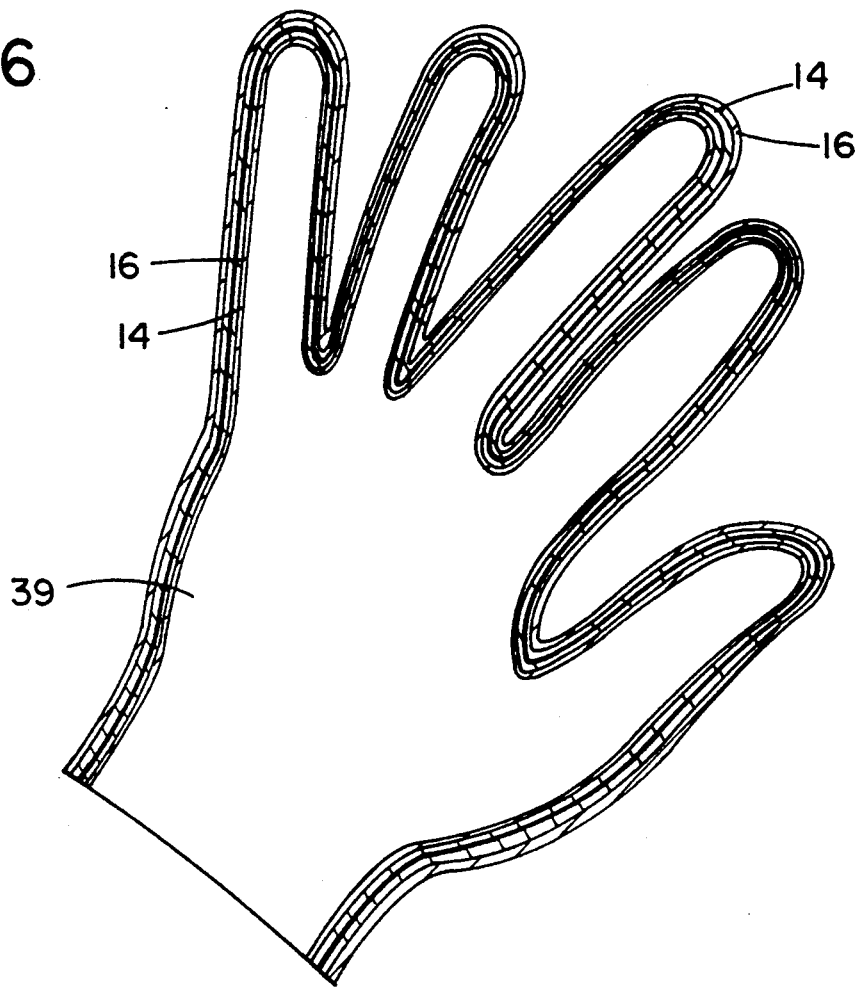
FIG. 6 is a plan view of the glove of this invention.

Referring to the drawings, FIGS. 1 and 2 illustrate a flexible bloodbag, generally denoted by the reference numbered 10, of the conventional size and shape employed for the transfer and storage of blood received from donors for subsequent transfusion to medical patients. The bloodbag 10 is formed of an outer sheet 11 of flexible plastic film such as polyvinyl chloride (PVC). Disposed on the internal surface 12 of sheet 11 is a coating of a hydrogel polymer 14. A solution of a viricide material 16 is absorbed in the hydrogel polymer 14 prior to or subsequent to the coating of the PVC film with the hydrogel polymer.

FIG. 3 illustrates bloodbag 10 after it has been partially filled with blood 18 from donor. Over time, viricide material 16 is leached from or drawn out of the hydrogel polymer 14 by the liquid blood 18 in contact therewith and diffuses throughout the blood 18 stored in bloodbag 10. This action may be enhanced by the conventional practice of mounting the filled bloodbag 10 on a rocker mechanism to maintain the stored blood under mild continuous agitation.

The viricide 16 inhibits HIV virions that may have been in the stored blood (i.e., the blood of the donor) so as to suppress their infectivity without injuring the red blood cell functions of the stored blood. While the inhibitory action of the viricide may be complete within a matter of hours, the coating 14 continuously releases additional viricide into the blood for as long as 30 days, or even more, so that the stored blood is under continuous protection from any latent infection of virus.

The viricide coated container of this invention is prepared by priming a substrate film 11, such as conventional plastic polyvinyl chloride (PVC) film, which is to be or has been formed into the container or bloodbag 10, so as to activate the film 11, and then coating the interior surface of the film 11 with a hydrogel polymer 14. A solution of viricide 16 is absorbed into the hydrogel polymer 14 prior to or after coating the film with the hydrogel polymer. The viricide 16 is released into the contents of the container or bloodbag 10 when the hydrogel polymer 14 is put in intimate contact with a liquid solution, such as blood, stored in the bloodbag 10.

The surface of the PVC film 11 which is or will define the interior surface of the container or bloodbag 10 of this invention is first primed so as to enable the coating of hydrogel polymer 14 to better bind thereto. Preferred conventional plastic film surface treatments which are effective for this purpose include flame, oxidizing acid, corona discharge or plasma. Of these treatments, corona discharge is the preferred priming treatment.

An alternative surface preparation treatment which may be performed prior to the coating of the substrate film 11 with the hydrogel polymer 14 is to coat the substrate film with a primer, a material which will activate the surface of the substrate film. This will ensure the adhesion of the hydrogel polymer to the substrate film. This primer may be a reactive resin, an oligomer in a solution suitable for ultraviolet (UV) or electron beam (EB) curing, or a solution of the salts of various polyvalent ions, such as cations (zinc, calcium, magnesium or aluminum) or anions (phosphates, sulfates or di- or tribasic organic acids). Such a primer would usually be applied to the substrate film and dried in place before applying the hydrogel polymer. While the primer is adequate to activate the surface of the substrate film without prior treatment of the substrate film by corona discharge, it may be desirable to apply both corona discharge treatment and a primer to suitably activate the surface of the substrate film so as to enable it to better bind the coating of hydrogel polymer.

The hydrogel polymer 14 used to coat the film 11 is preferably hydrophilic. Such hydrogel polymers may range from those which absorb 80–100% or more of water, based on their dry weight, and which become soft and spongy as a result, to those which will absorb only about 10% or less of their weight of water, remaining relatively firm even when saturated.

An advantage of using a low-absorbency hydrogel polymer to coat the substrate film is that compounds, such as the viricide, which are absorbed into the hydrogel polymer are released into liquids which come into intimate contact with the hydrogel polymer over a period of time. This is commonly referred to as time release action. High-absorbency hydrogel polymers release such compounds more rapidly, and may be advantageously employed where rapid release of the viricide is desired. Similarly, intermediate-absorbency hydrogel polymers will exhibit intermediate release rates.

The hydrogel polymer 14 used to coat the substrate film 11 is in the form of a liquid solution and may be applied to the activated surface of the substrate film by conventional coating methods, such as coating by roll, gravure, knife, dip or spray coating. The hydrogel polymer may also be printed onto the substrate film so as to provide a desired pattern of coverage. Once the film is coated, the hydrogel polymer is dried and cured in place so that a solid coating of suitable internal film strength and suitable adhesion to the substrate film develops.

The hydrogel polymer 14 may be applied by printing in a pattern such that, when the film 11 is die cut, the cut-out sections may be readily formed and sealed into pouches or bloodbags 10. The sealing may be accomplished by employing thermal or radio frequency (RF) heating equipment. For such sealing methods to be fully effective, it is desirable that the edge portions of the substrate film to be sealed are clean and free of hydrogel polymer. The printing method of applying the hydrogel polymer coating to the substrate film permits coating of only selected areas of the substrate film. Where desired, the printing method further permits application of adhesive coatings to selected edge areas of the sheet substrate film so that the substrate film can easily be formed into a bag.

The hydrogel polymers used in this invention are copolymers of hydroxyalkyl acrylates and/or methacrylates, and copolymers of acrylic and/or methacrylic acid. Other hydrogel polymers may incorporate mixtures of acrylic monomers, vinylpyrrolidone, itaconic or maleic acids, polyoxyethylene allyl ether and other hydrophilic monomers. Still other hydrogel polymers which may be used in this invention are polyurethane systems or cellulose ester systems. These hydrogel polymers may be applied to the substrate film as either organic solvent solutions or as aqueous solutions, and may include suitable cross-linking curing agents.

Where the viricide is to be used in contact with blood (e.g., in the hydrogel polymer of a bloodbag), it must not injure the red blood cell functions of the stored blood. Suitable viricides to be absorbed into the hydrogel polymer coating of this invention for use in contact with blood are urea derivatives, such as alkylureas or hydroxyureas. Only those viricides which do not affect red blood cell function should be used where the substance to be stored is blood. All conventional viricides may be used where the substance stored is not blood.

The effectiveness of the alkylureas in inhibiting HIV infectivity is related to the increased length of the alkyl chain of the urea molecule. Therefore, alkylureas may be administered as effective viricides. HIV infectivity is completely blocked when infective concentrations of HIV have been treated with a 0.2 mol solution of butylurea for a period of one hour.

Butylurea not only inactivates the HIV virions, but also inactivates intracellular HIV present in H9 cells and peripheral blood cells. Thus, treatment of red blood cells in a bloodbag with butylurea released from the hydrogel polymer coating of the internal bloodbag surface serves to inactivate HIV and prevent transmission of HIV from infected blood products in the bloodbag which may have been inadvertently donated by antibody-negative donors.

While butylurea is the alkylurea viricide of choice other alkylureas such as ethylurea and propylurea have demonstrated inhibition of HIV infectivity and may be employed as the viricide of this invention Hydroxyureas may also be used as the viricides of this invention. Hydroxyurea is a known cytostatic agent and has been shown to increase fetal hemoglobin production in sickle cell disease. Relatively low concentrations of hydroxyurea (0.5, 1 and 2 mM) suppress in vitro the expression of HIV in T cells and in T cell lines. As a result, hydroxyureas may be administered as effective viricides.

Finally, acetyl pyridium chloride, which is a quarternary ammonium surfactant, may be administered as an effective viricide, and may be used as the viricide absorbed into the hydrogel polymer of this invention.

It will be appreciated that the priming of one surface of the film and/or the application of hydrogel polymer to the primed surface may occur either while the film is in sheet form or in a container form. Indeed the film once in a container form may be inserted into an outer container for further strength, rigidity, etc.

A second embodiment of this invention, as shown in FIG. 4, is a loose pellet generally designated 32 consisting of a hydrogel polymer 34 installed inside a container 30. Alternatively, as shown in FIG. 5, a pellet generally designated 32A consisting of a polymer 37 is coated with a hydrogel polymer 34A and installed in container 30A. Pellets 32 and 32A are then each soaked in a solution of a viricide so as to absorb the viricide 36 into the hydrogel polymer 34, 34A. When a liquid medicine is subsequently added into the containers 30, 30A, the viricide is released into the medicine so as to inhibit activity of any virus or other microbial matter present in the container. Such use of a pellet 32, 32A provides long-term release of the viricide into the medicine or other liquid contents in the container. The use of a pellet is beneficial where the container has been previously opened for use or is opened for use over a period of time, such as eye drops. The hydrogel polymer 34 of pellet 32 and the polymer 37 and hydrogel polymer 34A of pellet 32A are preferably elastomeric so that they may be squeezed (i.e., substantially compressed) to fit through the opening 35 of a container 30, 30A where the opening 35 is of a smaller dimension than the respective nominal dimension of the pellet. In this manner, the pellet is retained in the container while the medicine or blood inside the container is poured out of the container from time to time—e.g., as the medicine is applied to a patient.

A third embodiment of the invention, as shown in FIG. 6, may be a flexible glove 39 wherein either or both of the inner and outer surfaces are coated with a hydrogel polymer 14 with a viricide 36 absorbed therein. The viricide 36 may then be released onto the skin of the hand of the wearer and/or released onto a surface contacted by the external surface of the glove so as to inhibit virus activity.

Figure 7:
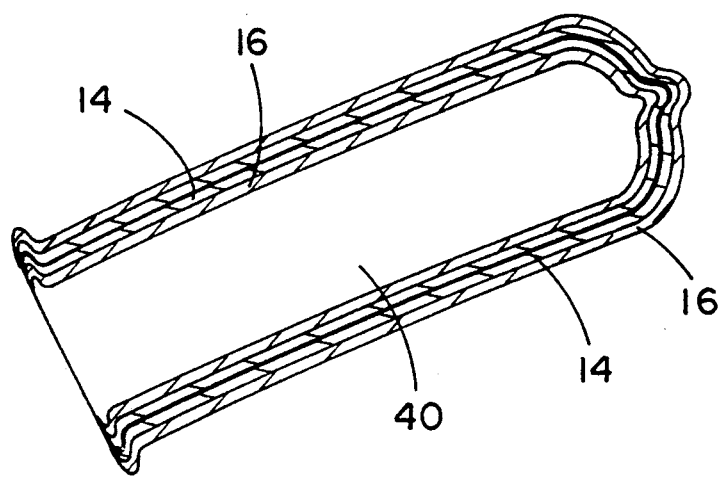
FIG. 7 is a plan view of the condom of this invention.

A fourth embodiment of the invention, as shown in FIG. 7, is a flexible condom 40, wherein either or both the inner and outer surfaces are coated with a hydrogel polymer 14 with a viricide 36 absorbed therein. The viricide 36 may then be released onto the skin of the wearer and/or released onto a surface contacted by the external surface of the condom so as to inhibit virus activity.

In a further alternative embodiment of the invention, a dilute solution of the viricide may be incorporated into the liquid hydrogel polymer subsequent to the coating of the substrate film with the hydrogel polymer, either prior to or subsequent to the curing of the hydrogel polymer to itself and to the substrate. This hydrogel polymer will release the viricide into an aqueous or non-aqueous solution which subsequently comes into contact with the hydrogel polymer.

EXAMPLE I

PVC film was treated with concentrated sulfuric acid and then rinsed thoroughly with water and dried. A coating of an acrylic resin hydrogel polymer, modified by incorporation of the cross-linking agent disclosed in U.S. Pat. No. 4,575,476, was applied to the film. The film was subsequently oven dried and cured at 120° C. for several minutes. The coating was smooth and even and displayed excellent wetting characteristics. The coating was also adherent and reasonably flexible, and displayed the absorbent qualities of hydrogel films.

EXAMPLE II

A similar procedure to that used in Example I was utilized in which the PVC film was pre-treated by exposure to an electrical field, as is found in corona discharge treatment, prior to being coated with the hydrogel polymer resin. Good wetting and spreading, film adherence and reasonable film flexibility were again observed, and the hydrogel polymer resin coating displayed the desired absorbent qualities.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention as defined in the appended claims.

We claim:

1. A method of preparing a viricide-coated container capable of time-release of such viricide upon contact with liquid contained in said container, which method comprises the steps of
   (a) priming at least a portion of a substrate film of which the container is made;
   (b) coating the primed portion of the substrate film with a liquid solution of hydrogel polymer and absorbing a viricide into the hydrogel polymer; and
   (c) forming the substrate film having the primed coated portion into a container having at least one closed end.

2. A method according to claim 1 including the step of absorbing the viricide into the hydrogel polymer subsequent to coating the substrate film with the hydrogel polymer.

3. A method according to claim 1 including the step of absorbing the viricide into the hydrogel polymer prior to coating the substrate film with the hydrogel polymer.

4. A method according to claim 1 wherein the substrate film which is primed and coated defines the interior surface of the container.

5. A method according to claim 1 wherein the substrate film which is primed and coated defines the exterior surface of the container.

6. A method according to claim 1 wherein the viricide is effective against HIV.

7. A method according to claim 1 wherein the substrate film is polyvinyl chloride film.

8. A method according to claim 1 wherein the substrate film is flexible and including the step of forming the primed coated substrate film into a container.

9. A method according to claim 1 wherein the substrate film is primed using a priming treatment.

10. A method according to claim 9 wherein the priming treatment is selected from the group consisting of flame, oxidizing acid, corona discharge or plasma.

11. A method according to claim 1 wherein the priming is performed by coating the substrate film with a primer.

12. A method according to claim 11 wherein the primer is selected from the group consisting of a reactive resin, an oligomer in solution suitable for ultraviolet or electron beam curing, and a salt solution of various polyvalent ions.

13. A method according to claim 12 wherein the polyvalent ions are cations.

14. A method according to claim 13 wherein the cations are selected from the group consisting of zinc, calcium, magnesium and aluminum.

15. A method according to claim 12 wherein the polyvalent ions are anions.

16. A method according to claim 15 wherein the anions are selected from the group consisting of phosphates, sulfates, di-basic organic acids and tri-basic organic acids.

17. A method according to claim 1 wherein the viricide is a urea derivative.

18. A method according to claim 17 wherein the urea derivative is a hydroxyurea.

19. A method according to claim 17 wherein the urea derivative is an alkylurea.

20. A method according to claim 19 wherein the alkylurea is butylurea.

21. A method according to claim 19 wherein the alkylurea is selected from the group consisting of ethylurea and propylurea.

22. A method according to claim 1 wherein the viricide is blood soluble, and does not adversely affect the red blood cell functions of blood.

23. A method according to claim 22 wherein the viricide is selected from the group consisting of alkylurea, hydroxyurea and combinations thereof.

24. A method according to claim 1 wherein the hydrogel polymer is a resin.

25. A method according to claim 1 wherein the hydrogel polymer is a copolymer of hydroxyalkyl acrylates and methacrylates.

26. A method according to claim 1 wherein the hydrogel polymer is a copolymer of acrylic and methacrylic acids.

27. A method according to claim 1 wherein the hydrogel polymer is a mixture of acrylic monomers, vinylpyrrolidone, acids selected from the group consisting of itaconic and maleic acids, polyoxyethylene allyl ether and hydrophilic monomers.

28. A method according to claim 1 wherein the hydrogel polymer is a cellulose ester system.

29. A method according to claim 1 wherein the hydrogel polymer is a polyurethane system.

30. A method according to claim 1 wherein the coating is performed by a method selected from the group consisting of coating by roll, gravure, knife, dip, print or spray.

31. A method according to claim 1 wherein the container is a bloodbag.

32. A method according to claim 1 wherein the container is a glove.

33. A method according to claim 1 wherein the container is a condom.

34. A method according to claim 1 wherein the liquid contained in said container is blood.

35. A viricide-coated container prepared by the method of claim 1.

36. A viricide-coated container capable of time-release of such viricide upon contact with liquid contents, comprising a primed substrate film defining a container having at least one closed end, and a hydrogel polymer coating disposed on the interior surface of the container, the hydrogel polymer coating containing a viricide.

37. A viricide-coated container according to claim 36 which is a bloodbag.

38. A viricide-coated container according to claim 36 which is a glove.

39. A viricide-coated container according to claim 36 which is a condom.

40. A viricide-coated insert suitable for insertion into a container having at least one closed end wherein the insert has been primed and subsequently coated with a viricide-containing hydrogel polymer such that the insert time-releases the viricide upon contact with liquid within the container.

41. The viricide-coated insert of claim 40 suitable for insertion in a compressed state into a container wherein the insert is comprised of a substantially compressible material that has been primed and subsequently coated with a viricide-containing hydrogel polymer such that the insert time-releases the viricide upon contact with liquid.

* * * * *